United States Patent
Kreischer et al.

(10) Patent No.: US 8,108,027 B2
(45) Date of Patent: Jan. 31, 2012

(54) COMBINED POSITRON EMISSION TOMOGRAPHY / MAGNETIC RESONANCE IMAGING APPARATUS

(75) Inventors: Ludwig Kreischer, Dormitz (DE); Jürgen Nistler, Erlangen (DE); Martin Rausch, Spardorf (DE); Wolfgang Renz, Erlangen (DE); Norbert Rietsch, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 776 days.

(21) Appl. No.: 12/213,656

(22) Filed: Jun. 23, 2008

(65) Prior Publication Data
US 2009/0005671 A1 Jan. 1, 2009

(30) Foreign Application Priority Data
Jun. 26, 2007 (DE) .......................... 10 2007 029 363

(51) Int. Cl.
*A61B 5/05* (2006.01)
(52) U.S. Cl. ......... 600/411; 600/407; 600/410; 600/422
(58) Field of Classification Search .................. 600/407, 600/410, 411, 422
See application file for complete search history.

(56) References Cited

U.S. PATENT DOCUMENTS

| | | | |
|---|---|---|---|
| 4,639,672 A | 1/1987 | Beaumont | |
| 4,939,464 A | 7/1990 | Hammer | |
| 5,744,959 A * | 4/1998 | Jeker et al. | 324/319 |
| 6,567,685 B2 * | 5/2003 | Takamori et al. | 600/410 |
| 2004/0061499 A1 | 4/2004 | Stocker | |
| 2005/0248951 A1* | 11/2005 | Hagen et al. | 362/382 |
| 2006/0251312 A1 | 11/2006 | Krieg et al. | |

FOREIGN PATENT DOCUMENTS
DE 10245942 A1 4/2004

* cited by examiner

*Primary Examiner* — Tse Chen
*Assistant Examiner* — Jason Ip
(74) *Attorney, Agent, or Firm* — Harness, Dickey & Pierce, P.L.C.

(57) ABSTRACT

A combined positron emission tomography/magnetic resonance imaging apparatus including a positron emission tomography apparatus having at least one radiation detector, and a magnetic resonance imaging apparatus having at least one gradient coil and a radio-frequency antenna device. At least one embodiment of the combined position emission tomography/magnetic resonance imaging apparatus is developed further in that a first molding is provided, whose surface coincides with the inner shell of the at least one gradient coil, and a second molding is provided, whose surface coincides with the outer shell of the radiation detector, the distance between the two shells being virtually constant over the circumference of the shells, and a vacuum seal being arranged in each case along at least a first and a second circumferential line such that a closed cavity is formed between the vacuum seals.

20 Claims, 2 Drawing Sheets

COMBINED POSITRON EMISSION TOMOGRAPHY / MAGNETIC RESONANCE IMAGING APPARATUS

PRIORITY STATEMENT

The present application hereby claims priority under 35 U.S.C. §119 on German patent application number DE 10 2007 029 363.3 filed Jun. 26, 2007, the entire contents of which is hereby incorporated herein by reference.

FIELD

Embodiments of the invention generally relate to a combined positron emission tomography/magnetic resonance imaging apparatus for imaging internal organs of an examination object.

BACKGROUND

Combining magnetic resonance (MR) examinations and positron emission tomography (PET) into one scanner with an identical imaging area is disclosed for example in U.S. Pat. No. 4,939,464. In this prior art, optical signals from a scintillation crystal are passed out of the measuring space to photodetectors via optical waveguides. The photodetectors are arranged outside the measuring space because they have to be protected from interactions with the magnetic fields required for the MR examinations.

Furthermore, DE 10 2005 015 070 discloses a combined positron emission tomography and magnetic resonance imaging scanner having a positron emission tomography scanner and a magnetic resonance imaging scanner. In the case of this prior art having the object of a very compact design, the positron emission tomography scanner part is arranged between a radio-frequency shield and a radio-frequency antenna device and is provided with shield cladding against radio-frequency radiation on the side of the radio-frequency antenna device.

When combining MR examinations with positron emission tomography, the structure with the PET scintillation crystals (PET gantry) must be arranged within the gradient coil of the MR system. Because the space available is extremely limited, the installation gap between the gradient coil and the PET construction is only a few millimeters wide.

This results in the problem that vibration of the surface of the gradient coil (a few 10 grams) is transferred to the PET gantry with almost no damping. This in turn leads to considerable loads on the PET gantry comprising the PET detectors, adhesively bonded crystal blocks and, possibly, sensitive electronics and plug connections which can be subjected to only a limited amount of mechanical stress.

DE 102 45 942 A1 discloses a magnetic resonance imaging scanner in which an internal pressure in a flexible hollow body between a boundary face of a cavity and a surface of a gradient coil system can be adjusted such that the gap can be sealed externally.

U.S. Pat. No. 4,639,672 discloses a nuclear magnetic resonance apparatus in which a sleeve is arranged within the gradient coils of the magnetic system, and forms a noise-absorbing shield between the gradient coils and the measurement space. Preferably, this is an evacuated space and a support for the gradient coils.

SUMMARY

In at least one embodiment of the invention, a combined positron emission tomography/magnetic resonance imaging apparatus is created in which even fewer mechanical oscillations are induced in the PET gantry by the magnetic resonance imaging apparatus.

At least one embodiment of the invention is based on evacuating the gap region between the gradient coil and the PET gantry (positron emission structure) so that this results in a low pressure therein. For this purpose, a connection between the body of the gradient coil and the PET gantry is established at two points and is in each case vacuum-tight but damps oscillations, so that a closed region which can be evacuated results between the two connection elements and the two bodies. The connection element is for example a silicone ring, and is preferably arranged at both ends of the gap region. When the vacuum has a residual pressure of less than 1 mbar, then both the transmission of oscillations and the transmission of heat by convection are suppressed very effectively. Preferably, the additional possibility of transmission of heat by radiation is prevented by inserting a thin superinsulation film into the gap region. So that the weight of the PET gantry is distributed as evenly as possible, at least one further vacuum seal is provided in the gap region between the first and the second vacuum seal, in order to subdivide the cavity and to support the moldings on each other.

Alternatively, an O-ring seal can be used as the vacuum-tight seal, and simultaneously takes over the support function for the PET gantry in the gradient coil.

The combined positron emission tomography/magnetic resonance imaging apparatus according to the invention, for imaging organs of an examination object in an examination space, which comprises a positron emission tomography apparatus having at least one radiation detector to detect positron annihilation radiation from the examination space, and a magnetic resonance imaging apparatus having at least one gradient coil to generate a magnetic gradient field in the examination space, and a radio-frequency antenna device to send excitation pulses into the examination space and to receive magnetic resonance signals from the examination space, the radiation detector and the at least one gradient coil being arranged coaxially and at virtually the same axial height around the examination space, a first molding being provided, whose surface coincides with the inner shell of the at least one gradient coil, and a second molding being provided, whose surface coincides with the outer shell of the radiation detector, the distance between the two shells being virtually constant over the circumference of the shells, and a vacuum seal being arranged in each case along a first and a second circumferential line such that a closed cavity is formed between the vacuum seals, is characterized in that at least one further vacuum seal is provided in the gap region between the first and the second vacuum seal in order to subdivide the cavity and to support the moldings on each other.

Preferably, an embodiment of the invention has at least one of the following further features:
the vacuum seals damp oscillations;
the vacuum seals are produced from silicone;
the vacuum seals are O-ring seals;
the vacuum seals are arranged at the ends of a gap region between the shells;
the vacuum seals are designed for a vacuum with a residual pressure of less than 1 mbar;
a superinsulation film is arranged in the gap region for shielding against electromagnetic radiation; and
the shells are in each case cylindrical.

One advantage of at least one embodiment of the invention is that no or only little heat transmission takes place from the magnetic resonance imaging apparatus to the PET gantry. In the prior art, convection heat of 500 W to 1000 W can flow from the gradient coil to the PET gantry, and the heat flow may vary depending on the activity of the gradient coil. However, the positron emission detectors require a temperature environment which is as constant as possible for reliable operation. This is ensured by a design according to at least one embodiment of the invention.

BRIEF DESCRIPTION OF THE DRAWINGS

Further features and advantages of the invention result from the following description of example embodiments, with reference to the attached drawings.

The drawings are not to scale. Identical elements and elements which act in the same manner are provided with the same reference symbols.

DETAILED DESCRIPTION OF THE EXAMPLE EMBODIMENTS

Figure 1:
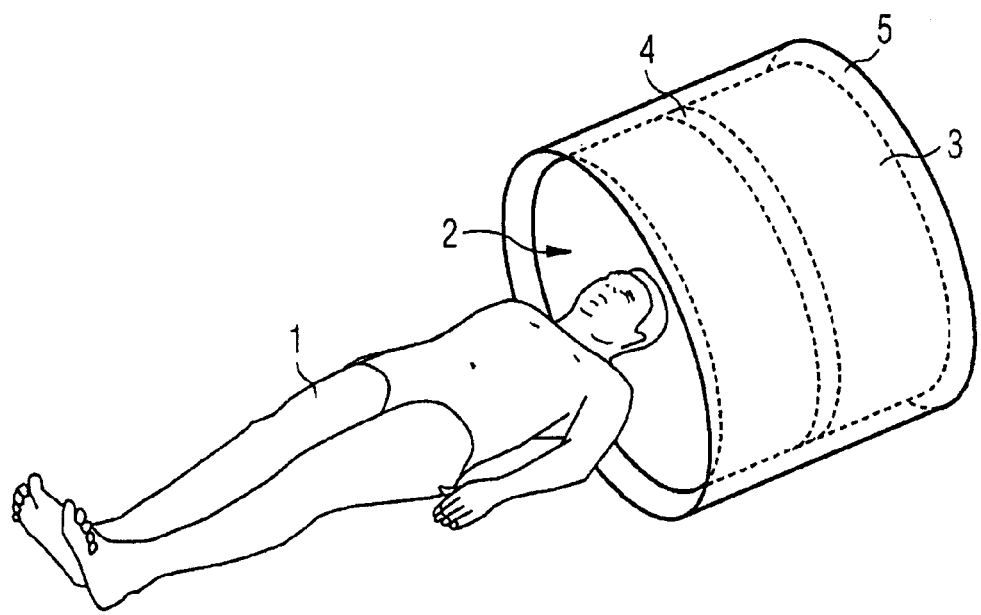
FIG. 1 schematically shows a perspective illustration of the basic design of a combined positron emission tomography/magnetic resonance imaging apparatus according to the prior art.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed, as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

As illustrated in FIG. 1, in the case of combined PET and MRI, an examination object 1 is moved into an examination space 2. This examination space 2 is surrounded by a PET apparatus 3 having a detector device 4. The detector device 4 is generally an arrangement of scintillation crystals (not shown) which are arranged annularly around the examination space 2. In the scintillation crystals, photons with an energy of 511 keV (annihilation radiation of the positrons) are converted to light quanta which in turn are then passed to photodetectors (not shown), preferably via optical waveguides (not shown) which generate electrical output signals as a function of the number of light quanta.

In order to improve the spatial resolution of the examination object 1 in the examination, the PET apparatus is surrounded by an MRI apparatus 5. This MRI apparatus 5 substantially comprises, in addition to a basic field magnet 6, a gradient coil 7 and a radio-frequency antenna device 8. These elements are explained in the following on the basis of FIG. 2.

Figure 2:
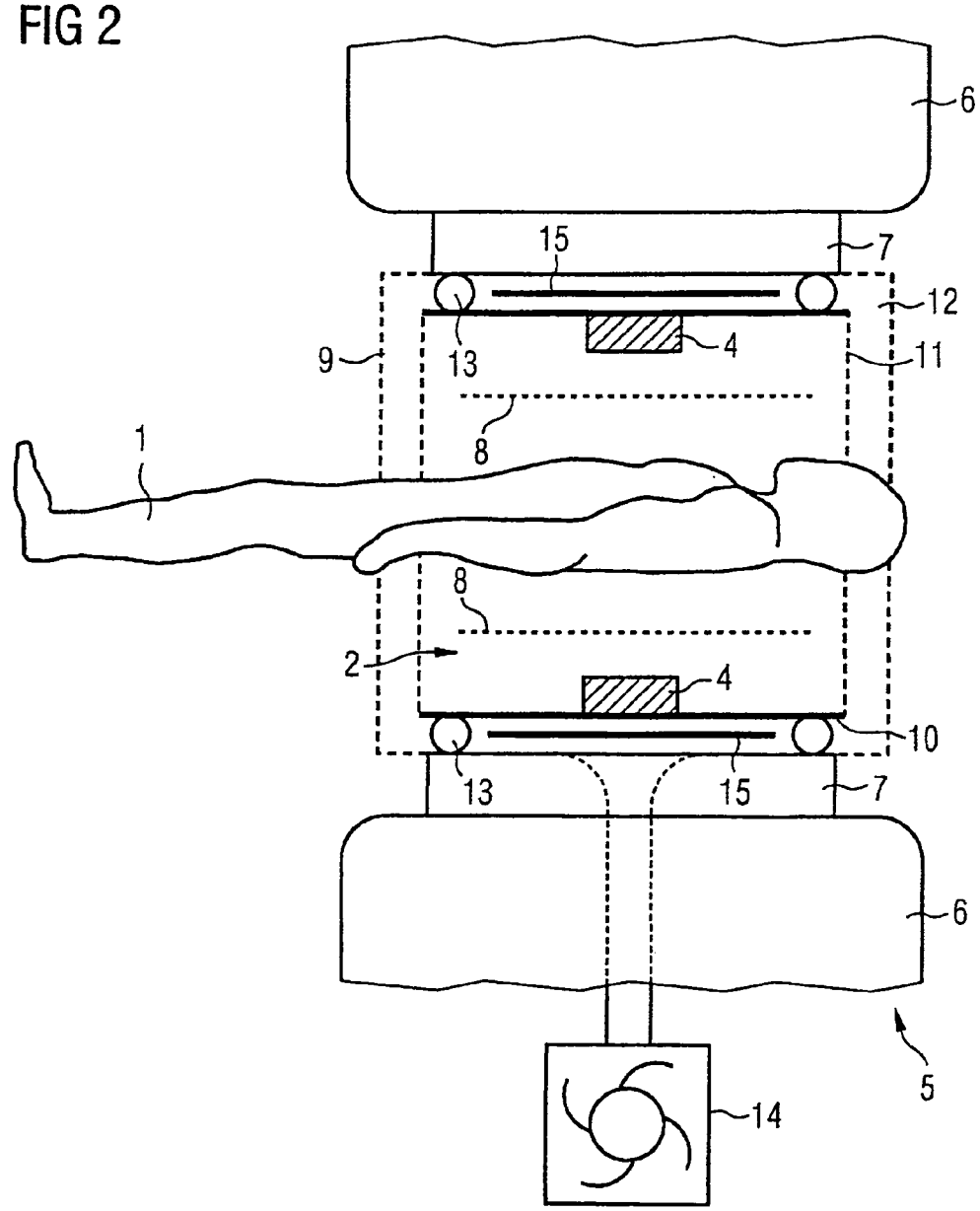
FIG. 2 schematically shows a cross section through one embodiment of the design according to an embodiment of the invention of a combined positron emission tomography/magnetic resonance imaging apparatus.

FIG. 2 illustrates such a design with further details in the form of a cross section. The examination object 1 is partially located within the examination space 2. The basic field magnetic coil 6 to generate a basic magnetic field is arranged completely externally around the examination space 2. The magnetic field generated by the coil 6 in the examination space 2 has an axis which coincides with the main axis of the examination object 2 on the imaging plane.

The gradient coil 7 is arranged within the coil 6 as a further coil with which a gradient field is generated in the examination space 2. The gradient coil 7 is wedged in or screwed to the basic magnetic field coil 6 so that the two coils 6 and 7 are fixedly connected to another.

A radio-frequency electromagnetic field is radiated into the examination space 2 by way of a radio-frequency antenna device 8 which is a part of the MRI apparatus.

The body of the gradient coil 7 defines an inner shell 9 which is the surface of that volume which is created (locally) by rotation of the innermost windings of the gradient coil about the central axis of the gradient coil 7, without "base" and "cover". The term "inner" relates here to the location of the shell 9 relative to the gradient coil 7. However, the shell 9 is of course located at the outer edge of the examination space 2.

The PET gantry 3 is arranged within the gradient coil 7 or, to be more precise, within the inner shell 9. As already described, the PET gantry 3 comprises as a substantial element for the present invention the annular scintillation crystal detector 4. An outer shell 11 is defined by means of the scintillation crystal detector 4. The term "outer" relates here to the location of the shell 11 relative to the scintillation crystal detector 4. However, the shell 11 is of course located within the MRI apparatus 5 and in particular within the inner shell 9.

In general, the two shells 9 and 11 are similar, that is to say they emerge from each other by means of a similarity transformation (central stretching in one or two directions).

In practice, the two shells 9 and 11 correspond to moldings. Thus, one molding is provided which coincides with the inner shell 9 on its side facing the examination space 2. This molding is the cast gradient coil 7 itself. Analogously, a molding 10 is provided which coincides with the outer shell 11 of the PET gantry 3. A gap region 12 is formed between the two moldings 7 and 10. In this case, in the axial direction, the molding 10 of the PET gantry 3 is shorter than or at most of equal length to the molding 7 of the MRI apparatus.

According to an embodiment of the invention, at least two vacuum seals 13 are arranged in the gap region 12 between the two moldings 7 and 10, and revolve around the molding 10 which surrounds the PET gantry. In other words, each vacuum seal 13 runs along a circumferential line of the molding 10. The vacuum seals 13 have thickness which suffices to close the gap between the molding 10 and the molding 7. This results in the creation of a air-tight sealed cavity between the moldings 7 and 13 and the two vacuum seals 13, and the cavity can be pumped out by a vacuum pump 14, so that pressure in the cavity is low. This ensures that oscillations of one molding cannot be transferred to the other molding via the air. In other words, the two moldings are acoustically decoupled from one another. In order to decrease the size of the respective cavities or to allow support the moldings 7 and 10 to be supported on each other by means of further vacuum seals, further vacuum seals 13 (not shown) can be provided in the gap region 12.

The vacuum seals 13 can in principle run about any desired axial position about the molding 10 of the PET apparatus. However, in one preferred embodiment of the PET/MRI apparatus according to the invention, the vacuum seals 13 are arranged at the opposite ends of the molding 10, as illustrated in FIG. 2. In this arrangement of the vacuum seals 13, it is possible to shield the scintillation crystals 4 of the PET gantry 3 against electromagnetic radiation over a large area. For this purpose, a superinsulation film 15 is provided in this embodiment, which is arranged between the first molding 10 and the second molding 7 and additionally between the two vacuum seals 13.

In general, what is meant by a local shell is that this does not have to be the shell of a rotational body in the strict sense, but can locally deviate therefrom, that is to say it can have minor dents. However, for example for reasons of the complexity of the production of the gradient coil body 7 and the PET gantry 3, it is advantageous if the shells 9 and 11 are actually in each case cylindrical overall.

Further, elements and/or features of different example embodiments may be combined with each other and/or substituted for each other within the scope of this disclosure and appended claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A combined positron emission tomography/magnetic resonance imaging apparatus for imaging organs of an examination object in an examination space comprising:
   a positron emission tomography apparatus including at least one radiation detector to detect positron annihilation radiation from the examination space; and
   a magnetic resonance imaging apparatus including,
      at least one gradient coil to generate a magnetic gradient field in the examination space,
      a radio-frequency antenna device to send excitation pulses into the examination space and to receive magnetic resonance signals from the examination space, the at least one radiation detector and the at least one gradient coil being arranged coaxially around the examination space, a first molding being provided, whose surface coincides with an inner shell of the at least one gradient coil, and a second molding being provided, whose surface coincides with an outer shell of the at least one radiation detector, a distance between the inner and outer shells being constant over a circumference of the shells,
      a first and a second vacuum seal being arranged along a respective first and a second circumferential line between the first molding and the second molding such that a closed cavity is formed between the first and second vacuum seals, and
      at least one further vacuum seal, provided in a gap region between the first and the second vacuum seals to subdivide the cavity and to support the moldings on each other.

2. The combined positron emission tomography/magnetic resonance imaging apparatus as claimed in claim 1, wherein at least one of the first, second and further vacuum seals damp oscillations.

3. The combined positron emission tomography/magnetic resonance imaging apparatus as claimed in claim 2, wherein at least one of the first, second and further vacuum seals are produced from silicone.

4. The combined positron emission tomography/magnetic resonance imaging apparatus as claimed in claim 1, wherein at least one of the first, second and further vacuum seals are O-ring seals.

5. The combined positron emission tomography/magnetic resonance imaging apparatus as claimed in claim 1, wherein at least one of the first, second and further vacuum seals are arranged at an end of a gap region between the shells.

6. The combined positron emission tomography/magnetic resonance imaging apparatus as claimed in claim 1, wherein at least one of the first, second and further vacuum seals are designed for a vacuum with a residual pressure of less than 1 mbar.

7. The combined positron emission tomography/magnetic resonance imaging apparatus as claimed in claim 1, wherein a superinsulation foil is arranged in the gap region for shielding against electromagnetic radiation.

8. The combined positron emission tomography/magnetic resonance imaging apparatus as claimed in claim 1, wherein the shells are cylindrical.

9. The combined positron emission tomography/magnetic resonance imaging apparatus as claimed in claim 2, wherein at least one of the first, second and further vacuum seals are arranged at an end of a gap region between the shells.

10. The combined positron emission tomography/magnetic resonance imaging apparatus as claimed in claim 2, wherein at least one of the first, second and further vacuum seals are designed for a vacuum with a residual pressure of less than 1 mbar.

11. The combined positron emission tomography/magnetic resonance imaging apparatus as claimed in claim 2, wherein a superinsulation foil is arranged in the gap region for shielding against electromagnetic radiation.

12. The combined positron emission tomography/magnetic resonance imaging apparatus as claimed in claim 2, wherein the shells are in each case cylindrical.

13. The combined positron emission tomography/magnetic resonance imaging apparatus as claimed in claim 3, wherein at least one of the first, second and further vacuum seals are arranged at an end of a gap region between the shells.

14. The combined positron emission tomography/magnetic resonance imaging apparatus as claimed in claim 3, wherein at least one of the first, second and further vacuum seals are designed for a vacuum with a residual pressure of less than 1 mbar.

15. The combined positron emission tomography/magnetic resonance imaging apparatus as claimed in claim 3, wherein a superinsulation foil is arranged in the gap region for shielding against electromagnetic radiation.

16. The combined positron emission tomography/magnetic resonance imaging apparatus as claimed in claim 3, wherein the shells are in each case cylindrical.

17. The combined positron emission tomography/magnetic resonance imaging apparatus as claimed in claim 4, wherein at least one of the first, second and further vacuum seals are arranged at an end of a gap region between the shells.

18. The combined positron emission tomography/magnetic resonance imaging apparatus as claimed in claim 4, wherein at least one of the first, second and further vacuum seals are designed for a vacuum with a residual pressure of less than 1 mbar.

19. The combined positron emission tomography/magnetic resonance imaging apparatus as claimed in claim 4, wherein a superinsulation foil is arranged in the gap region for shielding against electromagnetic radiation.

20. The combined positron emission tomography/magnetic resonance imaging apparatus as claimed in claim 4, wherein the shells are in each case cylindrical.

* * * * *